(12) United States Patent
Muramatsu et al.

(10) Patent No.: US 6,626,837 B2
(45) Date of Patent: Sep. 30, 2003

(54) ULTRASONOGRAPH

(75) Inventors: Hiroyuki Muramatsu, Chiba (JP); Masataka Shinogi, Chiba (JP); Hiroshi Odagiri, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/975,821

(22) Filed: Oct. 12, 2001

(65) Prior Publication Data

US 2002/0087082 A1 Jul. 4, 2002

(30) Foreign Application Priority Data

Nov. 27, 2000 (JP) ........................................ 2000-359292

(51) Int. Cl.⁷ ................................................ A61B 8/02
(52) U.S. Cl. ...................................................... 600/459
(58) Field of Search ................................. 600/459, 437, 600/462–471, 500–503; 310/334–336

(56) References Cited

U.S. PATENT DOCUMENTS

| | | | | |
|---|---|---|---|---|
| 3,552,382 A | * | 1/1971 | Mount | 73/628 |
| 4,068,521 A | * | 1/1978 | Cosentino et al. | 73/19 |
| 4,086,916 A | * | 5/1978 | Freeman et al. | 600/438 |
| 4,276,491 A | * | 6/1981 | Daniel | 310/335 |
| 4,966,152 A | * | 10/1990 | Gang et al. | 600/453 |
| 5,042,493 A | * | 8/1991 | Saito et al. | 600/459 |

* cited by examiner

Primary Examiner—Francis J Jaworski
(74) Attorney, Agent, or Firm—Adams & Wilks (57) ABSTRACT

An ultrasonograph capable of diagnosing a region with high sensitivity has a sensor provided with an ultrasound sending unit for sending ultrasound to the region and an ultrasound receiving unit for receiving ultrasound waves reflected from the region, a band for holding the sensor from a back side thereof relative to the diagnosed region and positioning a front side of the sensor against the diagnosed region, an information acquisition unit for acquiring information about the diagnosed region based on the reflected waves received by the ultrasound receiving unit, and an ultrasound-attenuating portion interposed between the sensor and the band for attenuating propagation of external noise from the band to the sensor and attenuating propagation of ultrasound signals through the band.

14 Claims, 7 Drawing Sheets

Prior Art

ULTRASONOGRAPH

BACKGROUND OF THE INVENTION

1. Field of the Invention

The present invention relates to an ultrasonograph such as a sphygmus (pulse wave) detection apparatus or ultrasonic imaging-and-diagnosing system for sending ultrasound to a region to be diagnosed (hereinafter often referred to as a region of interest) and obtaining information about the diagnosed region based on reflected waves and, more particularly, to an ultrasonograph capable of diagnosing a region of interest at high sensitivity.

2. Description of the Related Art

Ultrasonographs for obtaining information about a biological body or a substance using ultrasound have been well known for years. Such an ultrasonograph emits ultrasonic waves to a region of an examinee or substance to be diagnosed or examined, detects waves reflected from the diagnosed or examined region, and gains information about the diagnosed region based on the results of detection. For example, in a sphygmus detection apparatus using ultrasound, ultrasonic waves are emitted toward the radial artery of an examinee, and the pulse waveform or the pulse rate is derived from the amplitude of the reflected wave or from the variation in the frequency.

Figure 13:
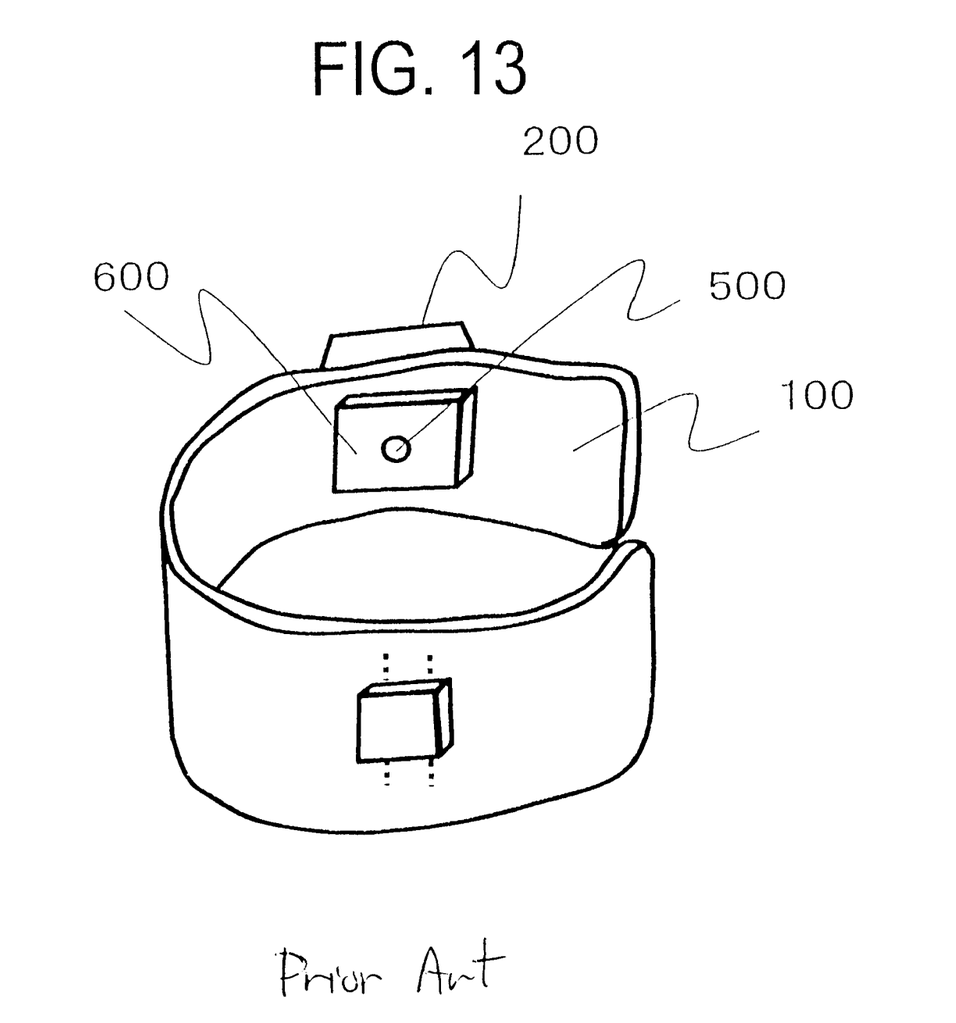
FIG. 13 is a perspective view of the related art ultrasonograph.

One example of such an ultrasonograph is shown in FIG. 13 and has a sensor portion 600 equipped with an ultrasound-sending unit and an ultrasound-receiving unit. The ultrasound-sending unit is applied against a region to be diagnosed and emits ultrasonic waves. The ultrasound-receiving unit receives reflected waves. The side of the sensor portion 600 that is applied against the diagnosed region and the opposite side are firmly bonded to a support unit 100 such as a belt with an adhesive or the like.

In ultrasonographic diagnosis, the sensor portion 600 is used while held against the surface of the diagnosed region of an examinee or the like by the support unit 100. The sensor portion 600 is applied against the diagnosed region directly or via a layer made of a material for acoustic matching such as silicon gel.

In this ultrasonograph, however, ultrasound is also emitted toward the support unit 100 from the ultrasound-sending unit of the sensor portion 600. The ultrasound sent toward the support unit 100 is reflected off the interface between the sensor portion 600 and the support unit 100, propagates through the support unit 100, and may be received as a noise signal by the ultrasound-receiving unit. Sometimes, external ultrasonic noise may propagate through the support unit 100 and be received by the ultrasound-receiving unit. Where the ultrasound-receiving unit receives a noise signal in this way, there arises the possibility that the detection sensitivity to information about the diagnosed region based on the received ultrasound is deteriorated.

SUMMARY OF THE INVENTION

Accordingly, it is an object of the present invention to provide an ultrasonograph capable of diagnosing a region of interest (i.e., a region to be diagnosed) at high sensitivity.

This object is achieved by an ultrasonograph in accordance with a first embodiment of the invention which comprises: a sensor portion having an ultrasound-sending unit for sending ultrasound to a region to be diagnosed and an ultrasound-receiving unit for receiving waves reflected from the diagnosed region; a support unit for holding the sensor portion from its back side relative to the diagnosed region; and an information acquisition unit for acquiring information about the diagnosed region based on the reflected waves received by the ultrasound-receiving unit. An ultrasound-attenuating portion for attenuating propagation of the ultrasound is interposed between the sensor portion and the support unit.

An ultrasonograph in accordance with a second embodiment of the present invention is based on the ultrasonograph in accordance with the first embodiment described above and characterized in that the aforementioned support unit is provided with a concave or cutout portion which is located opposite to the above-described sensor portion and concave when viewed from the sensor portion, and that the space between the sensor portion and the concave portion functions as the above-described ultrasound-attenuating portion.

An ultrasonograph in accordance with a third embodiment of the present invention is based on the ultrasonograph in accordance with the first embodiment described above and characterized in that the aforementioned ultrasound-attenuating portion is made of a material that attenuates propagation of ultrasound.

The above-described object is also achieved by an ultrasonograph in accordance with a fourth embodiment of the invention which comprises: a sensor portion having an ultrasound-sending unit for sending ultrasound to a region to be diagnosed and an ultrasound-receiving unit for receiving waves reflected from the diagnosed region; a support unit for holding the sensor portion from its back side relative to the diagnosed region, the support unit having a holding portion against which the sensor portion is held and an ultrasound-attenuating portion for attenuating propagation of ultrasound through the support unit, the ultrasound-attenuating portion being close to the holding portion; and an information acquisition unit for acquiring information about the diagnosed region based on the reflected waves received by the ultrasound-receiving unit.

An ultrasonograph in accordance with a fifth embodiment of the present invention is based on the ultrasonograph in accordance with the fourth embodiment, wherein the ultrasound-attenuating portion described above is a hollow groove formed in a surface of the support member that is on the side of the sensor portion.

An ultrasonograph in accordance with a sixth embodiment of the present invention is based on the ultrasonograph in accordance with the fourth embodiment, wherein the groove formed in the support member is filled with a material that attenuates propagation of ultrasound.

An ultrasonograph in accordance with a seventh embodiment of the present invention is based on the ultrasonograph in accordance with the third or sixth embodiment, wherein the material which attenuates propagation of ultrasound is epoxy resin containing powdered tungsten or a porous material.

DESCRIPTION OF THE PREFERRED EMBODIMENTS

One embodiment of the present invention is hereinafter described in detail by referring to FIGS. 1 to 5.

Figure 1:
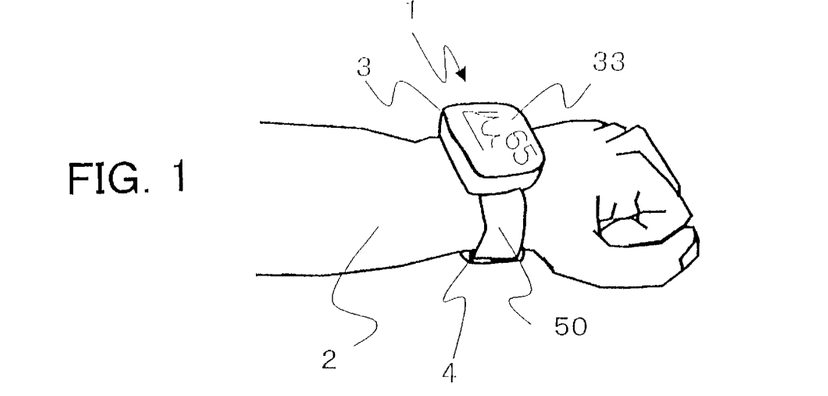
FIG. 1 is a perspective view of a sphygmus detection apparatus that is one form of an ultrasonograph in accordance with the present invention, and in which the apparatus is worn on an examinee.
Figure 2:
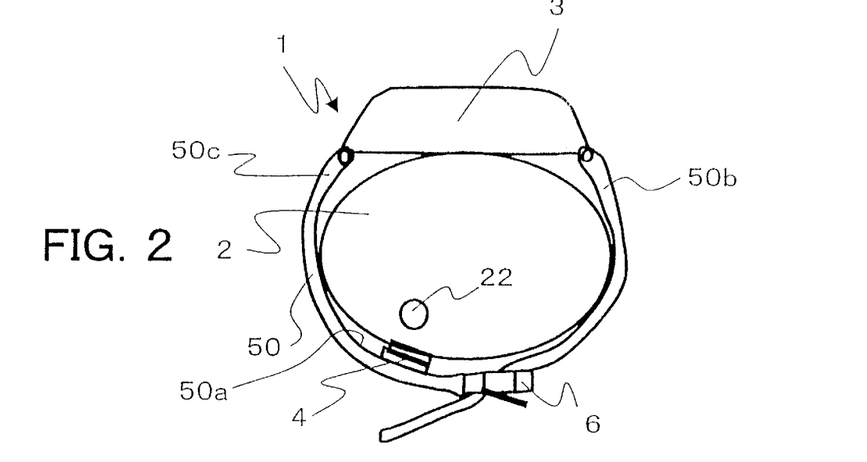
FIG. 2 is a side elevation of the sphygmus detection apparatus shown in FIG. 1, as viewed from the side of the shoulder joint of the examinee when the apparatus is worn on the examinee.

FIG. 1 is a perspective view of a sphygmus detection apparatus that is one form of an ultrasonograph in accordance with the present invention, and in which the apparatus is worn on an examinee. FIG. 2 is a side elevation of the sphygmus detection apparatus shown in FIG. 1, as viewed from the side of the shoulder joint of the examinee when the apparatus is worn on the examinee.

As shown in these FIGS. 1 and 2, the sphygmus detection apparatus in accordance with the present embodiment is indicated by numeral 1 and comprises a sensor portion 4 having a sending piezoelectric element and a receiving piezoelectric element, a belt 50 acting as a holding unit for holding the back side (i.e., the side of the sensor portion 4 facing away from the diagnosed region, the side facing away from the ultrasound-sending portion from which ultrasound is emitted toward the radial artery, and the side facing away from the side applied against the examinee) of the sensor portion 4 to the surface of the body outside the radial artery to hold the sensor portion 4 relative to the radial artery, and a processing portion 3 acting as an information acquisition unit for gaining the pulse waveform and the pulse rate at the radial artery based on the amplitude of the reflected waves received by the receiving piezoelectric element. The sending piezoelectric element of the sensor portion 4 acts as an ultrasound-sending unit for sending ultrasonic waves to the radial artery that is a region to be diagnosed. The receiving piezoelectric element acts as an ultrasound-receiving unit for receiving the ultrasonic waves reflected from the radial artery.

A space 62 acting as a portion for attenuating propagation of ultrasonic waves is interposed between the sensor portion 4 and the belt 50.

The sphygmus detection apparatus 1 in accordance with the present embodiment is now described in further detail.

As shown in FIG. 2, the belt 50 is split into two parts 50b and 50c. The processing portion 3 is connected between them. This belt 50 is wound around the examinee's wrist, and both ends of the belt are connected together by a fastening element 6. In this way, the belt is held around the examinee's wrist.

The processing portion 3 is equipped with a display portion 33 that is placed on the outer side of the belt 50 when it is worn. The sensor portion 4 is held against the inner surface 50a of the belt 50 when it is worn. When the processing portion 3 is attached to the left (or right) wrist 2 of the examinee on the hand's back, it follows that the sensor portion 4 is placed almost just over the radial artery 22 of the wearer and held there.

Figure 3:
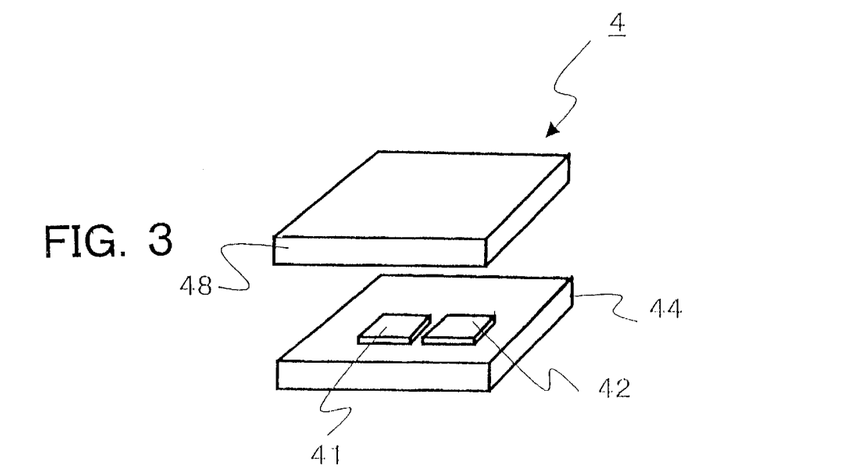
FIG. 3 is an exploded perspective view schematically showing the structure of the sensor portion.
Figure 4:
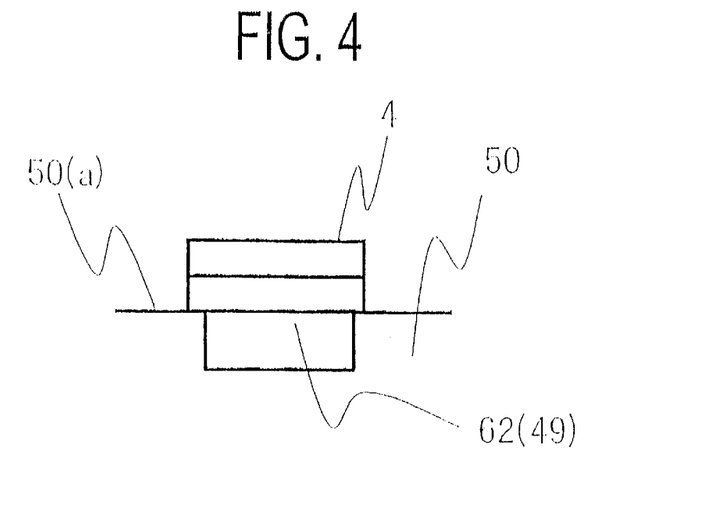
FIG. 4 is a cross section of the main portion of the sensor portion as viewed from the longitudinal direction of the belt, and in which the sensor portion is held to the belt.

FIG. 3 is an exploded perspective view schematically showing the structure of the sensor portion 4. FIG. 4 is a cross section as viewed from the longitudinal direction of the belt 50 under the condition where the sensor portion 4 is held to the belt 50.

As shown in FIG. 3, the sensor portion 4 comprises a lower substrate 44 having electrodes (not shown) and an upper substrate 48 similar in shape to the lower substrate 44. The upper substrate 48 is placed over the lower substrate 44. A pair of piezoelectric elements (a sending piezoelectric element 41 and a receiving piezoelectric element 42) are held between the lower substrate 44 and the upper substrate 48 and in contact with the electrodes of the lower substrate 44. The piezoelectric elements 41 and 42 are sandwiched between the lower substrate 44 and the upper substrate 48.

As shown in FIG. 4, the belt 50 has a concave or cutout portion 49 on one side of a thick-walled belt-like body, the concave portion being recessed on the side of the opposite surface. When the apparatus is worn, this concave portion 49 is on the side of the inner surface 50a.

The fringes of the sensor portion 4 are bonded to the periphery of the concave portion 49 in the belt 50 with adhesive, and the sensor portion 4 covers the concave portion 49. Thus, a space 62 is formed between the sensor portion 4 and the belt 50. This space 62 acts as an ultrasound-attenuating portion for attenuating propagation of ultrasound.

Any adhesive used to bond the sensor portion 4 to the belt 50 in the related art technique can be used without restriction as the adhesive for bonding the sensor portion 4 to the belt 50. In the present embodiment, glass is used as the upper substrate 48. It is also possible to apply epoxy resin or other material having an acoustic impedance midway between those of the human body and the piezoelectric elements (PZT or the like), taking account of the acoustic matching, instead of the upper substrate 48.

The sending piezoelectric element 41 receives a driver signal and sends amplitude-modulated ultrasound of 32 kHz toward the artery. Since the oscillation frequency is the same as the oscillation frequency of the watch in this way, if the sphygmus detection apparatus 1 is placed in the watch, the oscillator of the watch can be used in common. If necessary, it is amplified and delivered as an output. This can reduce the number of components of the sphygmus detection apparatus 1 and hence the apparatus can be fabricated inexpensively.

The sending piezoelectric element 41 and the receiving piezoelectric element 42 are connected with signal lines (not shown) buried in the belt 50 via the lower substrate 44 and the upper substrate 48, respectively. In the present embodiment, the sending piezoelectric element 41 and the receiving piezoelectric element 42 are prepared separately. One piezoelectric element may send, and the same piezoelectric element may receive reflected waves to be received after a given interval. Furthermore, plural piezoelectric elements or plural sets of piezoelectric elements may be used.

Figure 5:
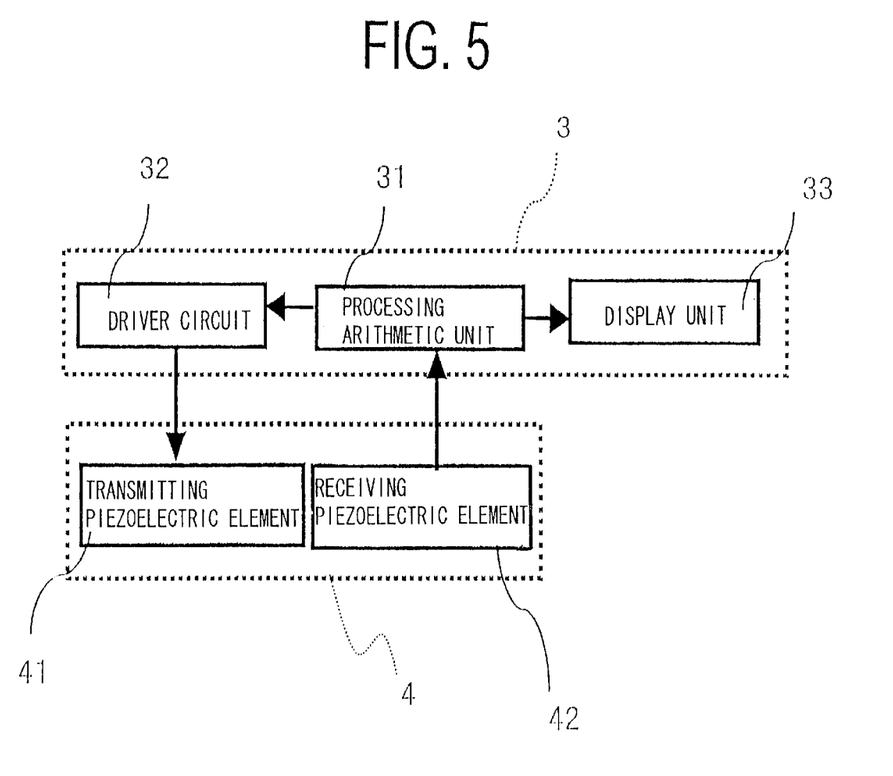
FIG. 5 is a block diagram showing the structure of the sphygmus detection apparatus shown in FIG. 1.

FIG. 5 is a block diagram showing the structure of the sphygmus detection apparatus 1 shown in FIG. 1.

As shown in this FIG. 5, the processing portion 3 comprises a driver circuit 32 for sending out a driver signal that activates the sending piezoelectric element 41, an arithmetic processing portion 31 for processing the signal based on the ultrasound received by the receiving piezoelectric element 42 to thereby obtain pulse waveform and pulse rate, and a display portion 33 for displaying the pulse waveform and pulse rate obtained by the arithmetic processing portion 31.

The driver circuit 32 is equipped with an oscillation source relying on an oscillator such as a quartz, and produces alternating current of a frequency corresponding to the natural frequency of the oscillator. High-frequency waves of 32 kHz are obtained by frequency-dividing the frequency of the alternating current by a factor of 2, 3, or so on. The high-frequency waves of 32 kHz are sent to the sending piezoelectric element 41 via a signal line to activate the sending piezoelectric element 41. This sending piezoelectric element 41 sends ultrasound toward the surface of the body of the wearer.

The arithmetic processing portion 31 detects the reception signal from the receiving piezoelectric element 42 that receives waves reflected from the radial artery, and creates a pulse-wave signal based on the detected reception signal. The time intervals between the peaks of the pulse-wave signal are measured such that the number of measurements is 3, 5, 7, or 10, for example. The number of pulses V per minute is found from the average time T of the measured time intervals according to the following formula (1).

$$V=60/T \tag{1}$$

It is to be noted that the method is not limited to the method of finding the number of pulses from the average time T between pulse waves. For instance, the number of pulses w existing within a given time interval t (e.g., 10 seconds) may be detected, and the number of pulses V per minute may be found according to the following equation (2).

$$V=w\times(60/t) \tag{2}$$

The pulse waveform and pulse rate obtained by the arithmetic processing portion 31 are sent to the display portion 33, where they are displayed. This display portion 33 is made of a liquid crystal display to visualize the pulse waveform and pulse rate. Alternatively, the pulse rate may be electrically displayed on a panel.

The sphygmus detection apparatus 1 of the structure described above is placed on the body surface during measurement of pulse waves such that the sensor portion 4 is almost above the radial artery 22. The apparatus 1 is held around the examinee's wrist 2 by tightening the belt 50.

Under this condition, if the power supply of the sphygmus detection apparatus 1 is turned on, the driver circuit 32 activates the sending piezoelectric element 41, which then sends ultrasound having a frequency of 32 kHz toward the radial artery 22. At this time, the ultrasound from the sending piezoelectric element 41 is also directed toward the outer surface but is attenuated and absorbed by the space.

The ultrasound radiated toward the radial artery 22 is reflected by the bloodstream through the radial artery 22. The ultrasound is attenuated and amplitude-modulated by the bloodstream. The degree of the amplitude modulation varies according to the blood pressure. Therefore, the reflected waves assume a waveform that is amplitude-modulated according to the blood pressure.

The reflected waves are received by the receiving piezoelectric element 42. Since the external ultrasound and so on propagate to this receiving piezoelectric element 42 via the belt 50, those components which propagate toward the sensor from outside the belt are attenuated and absorbed by the space 46.

In the receiving piezoelectric element 42, a reception signal is created based on the received reflected waves. This reception signal is sent to the arithmetic processing portion 31 of the processing portion 3 via a signal line (not shown) from the receiving piezoelectric element 42.

The arithmetic processing portion 31 detects the received signal in the same way as in normal AM detection. That is, rectification is done by a diode, and smoothing is done by a capacitor. Then, a detection signal is obtained as the voltage across a load resistor. Based on this detection signal, the pulse rate is counted, and a pulse-wave signal is created.

The pulse rate and pulse-wave signal counted by the arithmetic processing portion 31 are supplied to the display portion 33, where the pulse rate and pulse-wave signal are displayed. In the present embodiment, detection is done using AM detection. The frequency of the reflected waves varied by the Doppler effect of the bloodstream may be detected. In this case, the arithmetic processing portion 31 needs to be modified appropriately. In the present embodiment, a frequency of 32 kHz is used. The used frequency is not limited to this. Any frequency lying in the range of about 1 to 10 MHz may be employed.

In the sphygmus detection apparatus 1 in accordance with the present embodiment in this way, a mounting portion for mounting the sensor portion 4 of the belt is formed in a concave form. Therefore, a space is formed between the sensor portion 4 and the belt 50. Accordingly, ultrasound sent toward the belt 50 from the sensor portion 4 is attenuated and absorbed by the space 62. As a result, noise propagating from the sensor portion 4 to the belt 50 and received by the receiving piezoelectric element 42 is reduced.

Furthermore, ultrasound passing into the belt from the outside and traveling toward the sensor from outside the belt is attenuated and absorbed by the space 62. Accordingly, the noise received by the receiving piezoelectric element 42 is reduced in this respect, too.

Since the amount of noise received by the receiving piezoelectric element 42 is small, pulse wave information can be detected at high sensitivity based on the received signal.

It is to be noted that the present invention is not limited to the embodiment described above. Rather, various changes and modifications may be made within the scope delineated by the claims.

Figure 6A:
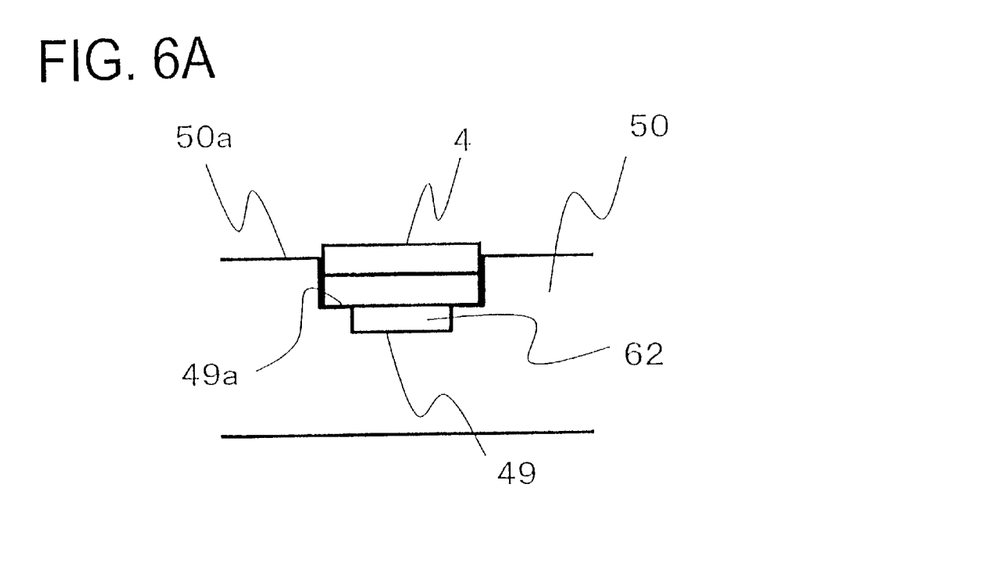
FIG. 6A is a cross-sectional view of the main portion of other ultrasonograph in accordance with the invention, taken from the longitudinal direction of the belt.
Figure 6B:
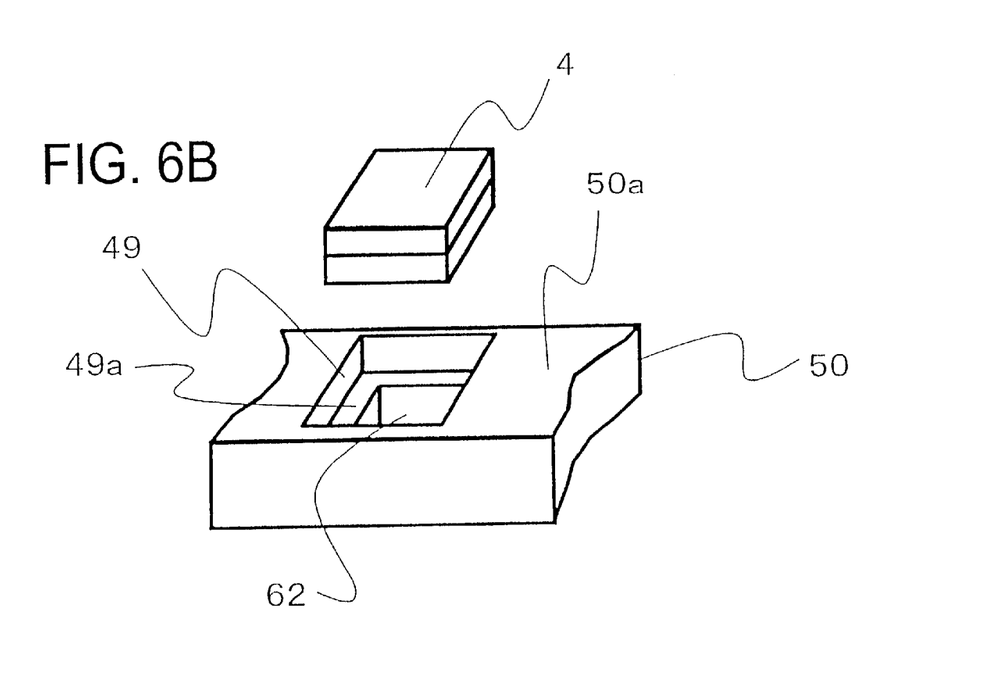
FIG. 6B is a perspective view of the main portion shown in FIG. 6A.

For example, in the above embodiment, the concave portion 49 is shaped into a form that is recessed one step from the outer surface of the belt 50. The sensor portion 4 is firmly fixed to the outer surface of the belt. The whole recessed portion 49 constitutes the space 62. It is to be noted that the shape of the recessed portion 49 is not limited to this. As shown in FIG. 6, the recessed portion 49 may be so shaped that it has an intermediate step portion 49a. The sensor portion 4 may be mounted on this step portion 49a. That portion of the recessed portion 49 which is closer to the bottom than the step portion 49a may form the space 62. By burying the sensor portion 4 partially into the recessed portion 49, the sensor portion 4 can be made to protrude by an appropriate amount without limiting the thickness of the sensor portion 4. The intensity of contact of the sensor portion 4 with the diagnosed region can be set to appropriate degree. Hence, the sensor portion 4 can be prevented from being applied against the diagnosed region with excessive or insufficient force; otherwise, the state of the diagnosed region would vary or the detection sensitivity to reflected light would deteriorate.

In the above-described embodiment and its modifications, the recessed portion 49 in the belt 50 forms the space 62. This space 62 acts as an ultrasound-attenuating portion. It is also possible to fabricate the ultrasound-attenuating portion from a material that attenuates propagation of ultrasound rather than from a space. For example, the recessed portion 49 in the above embodiment may be filled with epoxy resin containing powdered tungsten or a porous member consisting of a porous material, and this is used as the ultrasound-attenuating portion.

Figure 7:
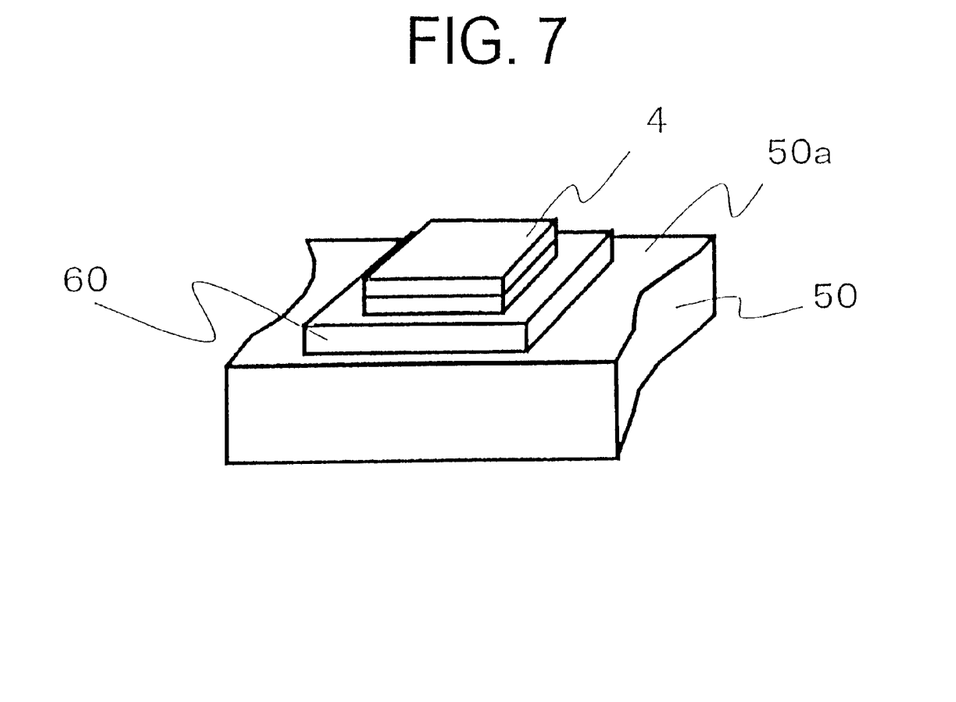
FIG. 7 is a perspective view of the main portion of a further ultrasonograph in accordance with the invention.

Furthermore, in the above-described embodiment and its modifications, the recessed portion 49 is formed in the belt, and the ultrasound-attenuating portion is formed by making use of this recessed portion 49. The recessed portion 49 may not be formed in the belt 50. As shown in FIG. 7, an ultrasound-attenuating member 60 made of a material that attenuates propagation of ultrasound may be held between the linearly extending belt 50 and the sensor portion 4, and this ultrasound-attenuating member 60 may be used as the ultrasound-attenuating portion. By forming the ultrasound-attenuating portion from the ultrasound-attenuating member 60 held between the belt 50 and the sensor portion 4, the ultrasound-attenuating portion is entirely interposed between the belt 50 and the sensor portion 4 and so any portion of the sensor portion 4 is not in direct contact with the belt 50. As a result, it is assured that ultrasound propagating through the belt 50 is attenuated and absorbed at the ultrasound-attenuating portion prior to entering the sensor portion 4, as well as the ultrasound reflected off the interface between the sensor portion 4 and the belt 50. Examples of material that attenuates propagation of ultrasound include epoxy region containing powdered tungsten and porous materials.

In addition, in the above-described embodiment and its modifications, the space 62 or the ultrasound-attenuating member 60 (ultrasound-attenuating portion) is interposed between the sensor portion 4 and the belt (support unit) 50. An ultrasound-attenuating portion for attenuating propagation of ultrasound through the belt 50 may be formed near the holding portion of the belt 50 to which the sensor portion 4 is held, together with or instead of the space 62 or ultrasound-attenuating member 60. Examples of such an ultrasonograph are illustrated in FIGS. 8–11.

Figure 8:
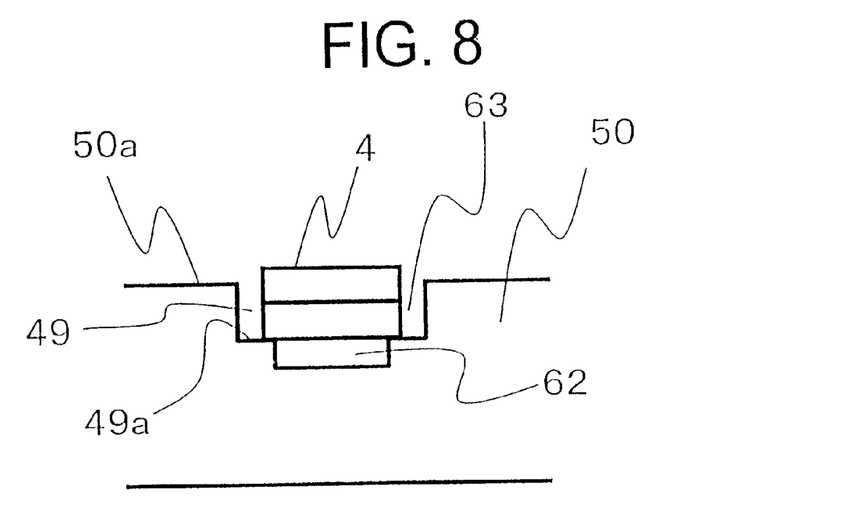
FIG. 8 is a cross section of the main portion of a still other ultrasonograph in accordance with the invention, taken from the longitudinal direction of the belt.

The modified example shown in FIG. 8 is based on the ultrasonograph shown in FIG. 6 and characterized as follows. The portion of the recessed portion 49 that lies from the side of the outer surface to the step portion 49a is made wider. The sensor portion 4 is mounted to the center of the widened portion. A space is formed between the outer surface of the recessed portion 49 and the sensor portion 4. This space is used as an ultrasound-attenuating portion (second ultrasound-attenuating portion) 63 for attenuating propagation of ultrasound through the belt. In this modified example shown in FIG. 8, ultrasound propagating along the inner surface 50a of the belt is attenuated and absorbed by the second ultrasound-attenuating portion 63. This prevents propagation to the sensor portion 4. Inconsequence, ultrasound noise produced by returning to the sensor portion 4 because of reflection at the interface between the sensor portion 4 and the belt 50 and noise entering the belt by reflection and entering from the outside can be well prevented from being received by the receiving piezoelectric element 42.

Figure 9:
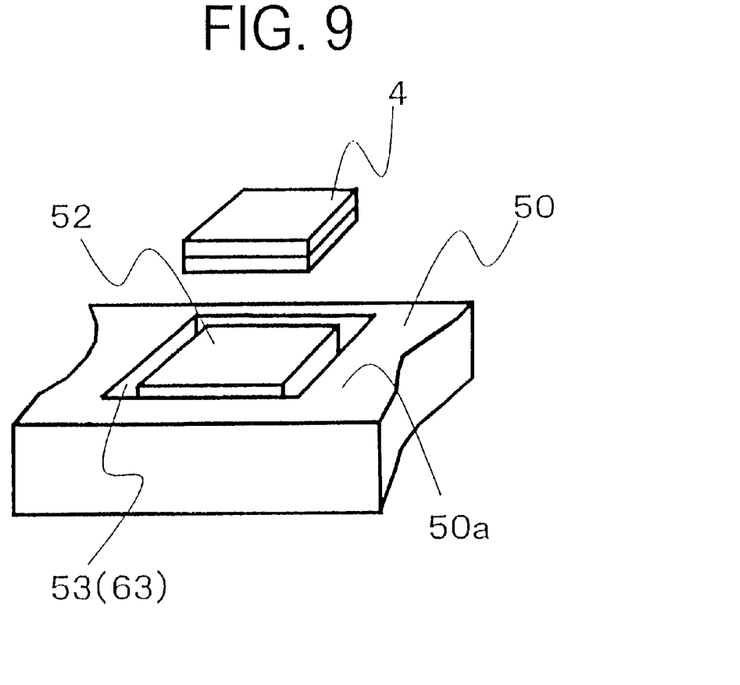
FIG. 9 is a perspective view of the main portion of an additional ultrasonograph in accordance with the invention.

In the modified example shown in FIG. 9, the sensor portion 4 is firmly bonded directly to the belt 50 with adhesive. A groove 53 is formed around the holding portion 52 of the belt that holds the sensor portion 4. The space within the groove 53 forms the ultrasound-attenuating portion 63. In the modified example shown in FIG. 10, the sensor portion 4 is directly firmly bonded to the belt 50 with adhesive. Grooves 53 extending across the belt 50 are formed near the holding portion of the belt 50 which holds the sensor portion 4. The spaces inside the grooves 53 constitute an ultrasound-attenuating portion. The spaces may be directly used as the ultrasound-attenuating portion. The spaces may also be filled with epoxy resin containing powdered tungsten or a porous material for attenuating ultrasound to form an ultrasound-attenuating portion, in the same way as in other embodiments.

Figure 10:
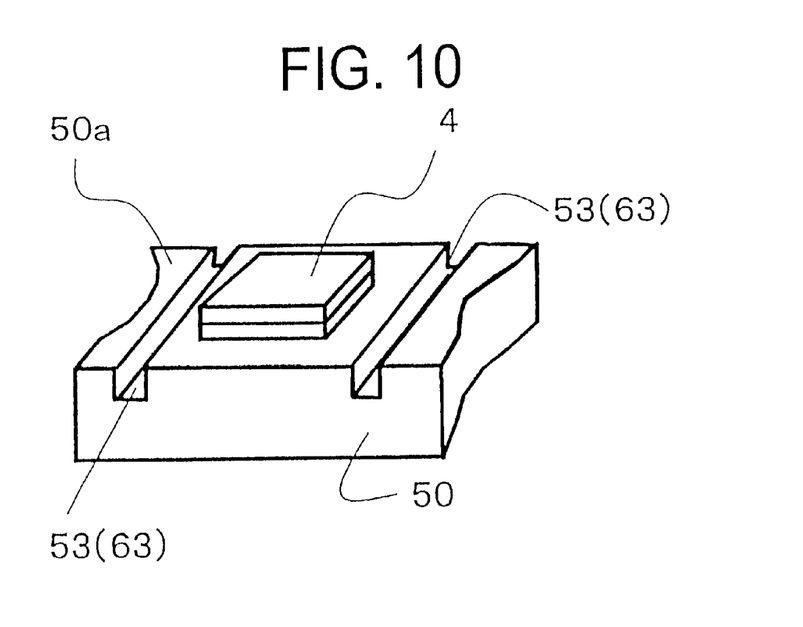
FIG. 10 is a perspective view of the main portion of a still other ultrasonograph in accordance with the invention.

By forming the space 63 for attenuating propagation of ultrasound through the belt (support unit) 50 near the holding portion of the belt (support unit) 50 to which the sensor portion 4 is held as in the modified embodiment shown in FIG. 9 and the modified embodiment shown in FIG. 10, noise entering the belt 50 by reflection at the interface between the sensor portion 4 and the belt 50 and noise entering from the outside are prevented from propagating through the belt 50; otherwise, the noise would be received by the receiving piezoelectric element 42. Hence, the apparatus can diagnose the region of interest at high sensitivity.

Figure 11:
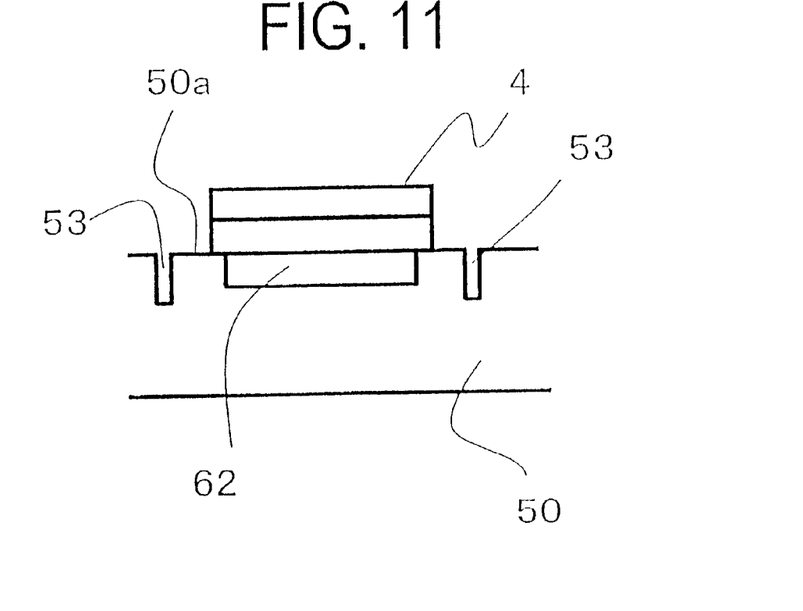
FIG. 11 is a cross section of the main portion of a yet other ultrasonograph in accordance with the invention, taken from the longitudinal direction of the belt.

The modified embodiment shown in FIG. 11 is based on the embodiment already described in connection with FIGS. 1–5 and characterized in that a groove 53 extending across the belt 50 is formed near the holding portion to which the sensor portion 4 is held to make the space within the groove 53 the second ultrasound-attenuating portion, in the same way as in FIG. 10. Also in this modified embodiment, ultrasonic noise produced by returning to the sensor portion 4 by reflection at the interface between the sensor portion 4 and the belt 50 and noise entering the belt by reflection and noise entering from the outside can be well prevented from being received by the receiving piezoelectric element 42, in the same way as in the modified embodiment shown in FIG. 8.

Figure 12:
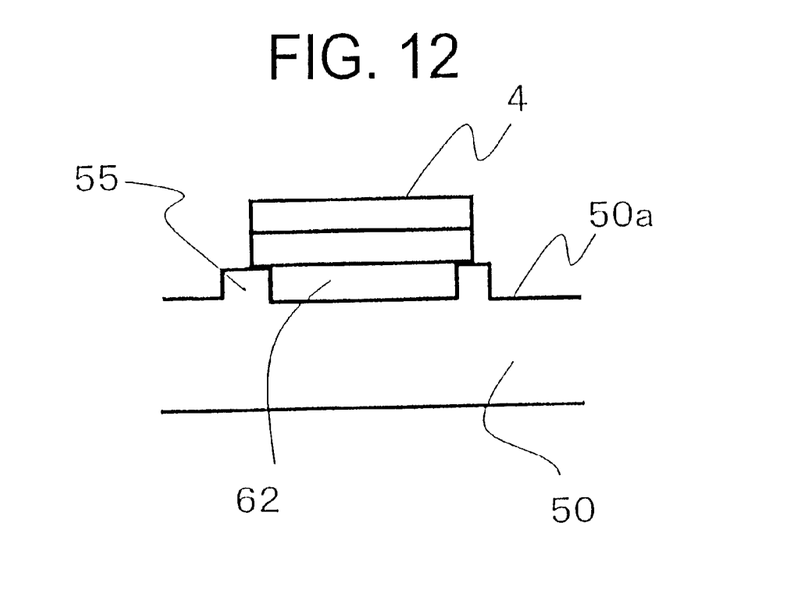
FIG. 12 is a cross section of the main portion of a further ultrasonograph in accordance with the invention.

In the above-described embodiments and modifications, the recessed portion 49 is formed on the side of the inner surface 50a of the belt 50 to which the sensor portion 4 is held to place the ultrasound-attenuating portion between the sensor portion 4 and the belt 50. Where the ultrasound-attenuating portion is placed between the sensor portion 4 and the belt 50, one or more protrusions 55 may be formed on the side of the inner surface 50a of the belt 50 without forming the recessed portion 49 in the inner surface 50a of the belt 50. The sensor portion 4 may be held to this protrusion 55. Thus, the space 62 may be formed between the sensor portion 4 and the belt 50. This space may be used as an ultrasound-attenuating portion directly or by filling the space with a material that attenuates ultrasound. Two such protrusions 55 may be formed across the belt, or may be cylindrical form such as rectangular form whose dimensions are smaller than those of the sensor portion 4.

In the above-described embodiments and modifications, the ultrasonograph is a sphygmus detection apparatus. The ultrasonograph to which the present invention is applied is not limited to sphygmus detection apparatus. The ultrasonograph in accordance with the present invention only needs to comprise: a sensor portion having an ultrasound-sending unit for sending ultrasound to a region to be diagnosed and an ultrasound-receiving unit for receiving the ultrasound reflected from the diagnosed region; a support unit for holding and supporting the sensor portion from its back side relative to the diagnosed region; and an information acquisition unit for acquiring information about the diagnosed region based on the reflected waves received by the ultrasound-receiving unit. For example, the ultrasonograph can be an imaging-and-diagnosing apparatus for obtaining an image of the inside of the human body by ultrasound, an ultrasonic flaw detector for ultrasonically searching a building or the like for damages, and various kinds of measuring instruments.

The aforementioned modifications can be used in combination if necessary.

As described thus far, the ultrasonograph in accordance with the present invention can diagnose a region of interest with reduced ultrasonic noise and thus at high sensitivity.

What is claimed is:

1. An ultrasonograph comprising:
    a sensor having an ultrasound sending unit for sending ultrasound to a region to be diagnosed and an ultrasound receiving unit for receiving ultrasound waves reflected from the diagnosed region;
    a band for holding the sensor from a back side thereof relative to the diagnosed region and positioning a front side of the sensor against the diagnosed region;
    an information acquisition unit for acquiring information about the diagnosed region based on the reflected waves received by the ultrasound receiving unit; and
    an ultrasound-attenuating portion interposed between the sensor and the band for attenuating propagation of external noise from the band to the sensor and attenuating propagation of ultrasound signals through the band, the ultrasound-attenuating portion comprising a recess formed in the band opposite the sensor and recessed relative to the sensor to define an empty space between the sensor and the recessed portion.

2. An ultrasonograph according to claim 1; wherein the band is a wrist band mountable to a user's wrist for positioning the sensor over an artery in the user's wrist.

3. An ultrasonograph comprising:
    a sensor having an ultrasound sending unit for sending ultrasound to a region to be diagnosed and an ultrasound receiving unit for receiving waves reflected from the diagnosed region;
    a band for holding the sensor from a back side thereof relative to the diagnosed region and positioning a front side of the sensor against the diagnosed region, the band having a holding portion against which the sensor is held and an ultrasound-attenuating portion proximate the holding portion for attenuating propagation of external noise from the band to the sensor and attenuating propagation of ultrasound signals through the band, the ultrasound-attenuating portion comprising a hollow groove formed in a surface of the band at a side of the sensor; and
    an information acquisition unit for acquiring information about the diagnosed region based on the reflected waves received by the ultrasound receiving unit.

4. An ultrasonograph according to claim 3; wherein the band is a wrist band mountable to a user's wrist for positioning the sensor over an artery in the user's wrist.

5. An ultrasonograph comprising: a wrist band; a sensor mounted to the wrist band so as to be positionable against a user's wrist and having a sensor for emitting an ultrasound signal toward an artery in the user's wrist and receiving an ultrasound signal reflected by blood flowing in the artery; an ultrasound-attenuating portion interposed between the sensor and the wrist band for attenuating noise from propagating from the wrist band to the sensor and attenuating ultrasound signals propagating toward the wrist band, the ultrasound-attenuating portion comprising a recess formed in the wrist band opposite the sensor and recessed relative to the sensor such that a space is provided between the sensor and the recess; and a processing unit for acquiring pulse wave information from the ultrasound signal received by the senor.

6. An ultrasonograph according to claim 5; wherein the pulse wave information acquired by the processing unit comprises the user's pulse rate.

7. An ultrasonograph according to claim 5; further comprising a display for displaying the pulse wave information.

8. An ultrasonograph according to claim 5; wherein the sensor comprises at least one piezoelectric element for emitting and receiving the ultrasound signal.

9. An ultrasonograph according to claim 8; wherein the sensor further comprises a substrate on which the at least one piezoelectric element is mounted, the substrate being mounted to the wrist band such that the ultrasound-attenuating portion is interposed between the substrate and the wrist band, and a material covering the at least one piezoelectric element.

10. An ultrasonograph according to claim 9; wherein the material covering the at least one piezoelectric element comprises glass or an epoxy resin.

11. An ultrasonograph according to claim 8; wherein the sensor comprises a sending piezoelectric element for sending the ultrasound signal and a receiving piezoelectric element for receiving the ultrasound signal.

12. An ultrasonograph according to claim 5; further comprising a housing mounted to the wrist band and containing therein the processing unit.

13. An ultrasonograph according to claim 12; further comprising a timepiece movement contained in the housing.

14. An ultrasonograph according to claim 13; further comprising a display for displaying the pulse information and a current time output by the timepiece movement.

* * * * *